US00PP23319P2

(12) United States Plant Patent
Pieters

(10) Patent No.: US PP23,319 P2
(45) Date of Patent: Jan. 8, 2013

(54) ***CHRYSANTHEMUM* PLANT NAMED 'BRONZE SAN REMO RUNNER'**

(50) Latin Name: *Chrysanthemum×morifolium*
Varietal Denomination: Bronze San Remo Runner

(75) Inventor: Luc Remi Johan Pieters, Staden-Oostnieuwkerke (BE)

(73) Assignee: Pieters Joseph & Luc B.V.B.A., Staden-Oostnieuwkerke (BE)

( * ) Notice: Subject to any disclaimer, the term of this patent is extended or adjusted under 35 U.S.C. 154(b) by 40 days.

(21) Appl. No.: 13/066,463

(22) Filed: Apr. 14, 2011

(51) Int. Cl.
*A01H 5/00* (2006.01)

(52) U.S. Cl. ..... Plt./290

(58) Field of Classification Search ..... Plt./290
See application file for complete search history.

(56) References Cited

OTHER PUBLICATIONS

UPOV-PLUTO Plant Variety Database, 2012-02, cultivar name 'Bronze San Remo Runner'.*

* cited by examiner

*Primary Examiner* — Susan McCormick Ewoldt
(74) *Attorney, Agent, or Firm* — C. A. Whealy

(57) ABSTRACT

A new and distinct cultivar of *Chrysanthemum* plant named 'Bronze San Remo Runner', characterized by its uniform, upright, outwardly spreading and rounded plant habit; moderately vigorous growth habit; freely branching habit; dense and full plant habit; freely flowering habit; large decorative-type inflorescences with greyed orange-colored ray florets; long flowering period; and excellent garden performance.

2 Drawing Sheets

Botanical designation: *Chrysanthemum×morifolium.*
Cultivar denomination: 'BRONZE SAN REMO RUNNER'.

CROSS-REFERENCED TO CLOSELY-RELATED APPLICATIONS

Title: *Chrysanthemum* Plant Named 'Dark San Remo Runner'.
Applicant: Luc Remi Pieters.
Filed: Concurrently with this application Ser. No. 13/066,466.

BACKGROUND OF THE INVENTION

The present invention relates to a new and distinct cultivar of *Chrysanthemum* plant, botanically known as *Chrysanthemum×morifolium* and hereinafter referred to by the name 'Bronze San Remo Runner'.

The new *Chrysanthemum* plant is a naturally-occurring whole plant mutation of *Chrysanthemum×morifolium* 'San Remo Runner', not patented. The new *Chrysanthemum* plant was discovered and selected by the Inventor as a flowering plant from within a population of plants of 'San Remo Runner' in a controlled greenhouse environment in Staden-Oostnieuwkerke, Belgium in October, 2007.

Asexual reproduction of the new *Chrysanthemum* plant by vegetative cuttings was first conducted in a controlled greenhouse environment in Staden-Oostnieuwkerke, Belgium in February, 2008. Asexual reproduction by cuttings has shown that the unique features of this new *Chrysanthemum* plant are stable and reproduced true to type in successive generations.

SUMMARY OF THE INVENTION

Plants of the new *Chrysanthemum* have not been observed under all possible environmental conditions and cultural conditions. The phenotype may vary somewhat with variations in environment such as temperature, daylength and light intensity, without, however, any variance in genotype.

The following traits have been repeatedly observed and are determined to be the unique characteristics of 'Bronze San Remo Runner'. These characteristics in combination distinguish 'Bronze San Remo Runner' as a new and distinct *Chrysanthemum* plant:

1. Uniform, upright, outwardly spreading and rounded plant habit; moderately vigorous growth habit.
2. Freely branching habit; dense and full plant habit.
3. Freely flowering habit.
4. Large decorative-type inflorescences with greyed orange-colored ray florets.
5. Long flowering period.
6. Excellent garden performance.

Plants of the new *Chrysanthemum* differ primarily from the parent, 'San Remo Runner', in ray floret color as plants of 'San Remo Runner' have dark pink-colored ray florets.

Plants of the new *Chrysanthemum* can be compared to plants of *Chrysanthemum×morifolium* 'Tardel', not patented. In side-by-side comparisons conducted in Staden-Oostnieuwkerke, Belgium, plants of the new *Chrysanthemum* differed from plants of 'Tardel' in the following characteristics:

1. Plants of the new *Chrysanthemum* flowered earlier than plants of 'Tardel'.
2. Plants of the new *Chrysanthemum* had decorative type inflorescences whereas plants of 'Tardel' had daisy type inflorescences.
3. Plants of the new *Chrysanthemum* and 'Tardel' differed in ray floret color as plants of 'Tardel' had yellow-colored ray florets.
4. Plants of the new *Chrysanthemum* were not susceptible to Rust pathogens whereas plants of 'Tardel' were susceptible to Rust pathogens.

Plants of the new *Chrysanthemum* can also be compared to plants of *Chrysanthemum×morifolium* 'Dark San Remo Runner', disclosed in a U.S. Plant Patent application filed concurrently. In side-by-side comparisons conducted in Staden-Oostnieuwkerke, Belgium, plants of the new *Chrysanthemum* differ primarily from plants of 'Dark San Remo Runner' in ray floret color.

BRIEF DESCRIPTION OF THE PHOTOGRAPHS

The accompanying photographs illustrate the overall appearance of the new *Chrysanthemum* plant showing the colors as true as it is reasonably possible to obtain in colored reproductions of this type. Colors in the photographs may differ slightly from the color values cited in the detailed botanical description which accurately describe the colors of the new *Chrysanthemum* plant.

The photograph on the first sheet comprises a side perspective view of a typical flowering plant of 'Bronze San Remo Runner' grown in a container.

The photograph on the second sheet are close-up views of the upper and lower surfaces of typical inflorescences (left) of 'Bronze San Remo Runner' and upper and lower surfaces of typical leaves (right) of 'Bronze San Remo Runner'.

DETAILED BOTANICAL DESCRIPTION

The aforementioned photographs and following observations and measurements describe plants grown during the summer and autumn in 19-cm containers in an outdoor nursery in Staden-Oostnieuwkerke, Belgium and under conditions and practices which approximate those generally used in commercial *Chrysanthemum* production. During the production of the plants, day temperatures ranged from 10° C. to 25° C. and night temperatures ranged from 5° C. to 15° C. Plants were 5.5 months old when the photographs and description were taken. In the following description, color references are made to The Royal Horticultural Society Colour Chart, 2007 Edition, except where general terms of ordinary dictionary significance are used.

Botanical classification: *Chrysanthemum×morifolium* 'Bronze San Remo Runner'.

Parentage: Naturally-occurring whole plant mutation of *Chrysanthemum×morifolium* 'San Remo Runner', not patented.

Propagation:

*Type*.—Terminal vegetative cuttings.

*Time to initiate roots, summer*.—About 14 days at temperatures of about 20° C.

*Time to initiate roots, winter*.—About 20 days at temperatures of about 20° C.

*Time to produce a rooted young plant, summer*.—About 30 days at temperatures of about 20° C.

*Time to produce a rooted young plant, winter*.—About 40 days at temperatures of about 20° C.

*Root description*.—Fine, fibrous; light brown in color.

*Rooting habit*.—Freely branching; medium density.

Plant description:

*Appearance*.—Perennial *Chrysanthemum* with decorative type inflorescences; stems upright and outwardly spreading giving a uniformly rounded appearance to the plant; very freely branching habit with about 30 lateral branches developing per plant; pinching enhances lateral branch development; dense and full plant habit; moderately vigorous growth habit.

*Plant height*.—About 39 cm.

*Plant width*.—About 68 cm.

*Lateral branches*.—Length: About 22.5 cm. Diameter: About 4 mm. Internode length: About 2.1 cm. Strength: Strong. Aspect: Lateral branches positioned about 40° from the main stem. Texture: Densely pubescent; longitudinally ridged. Color: Close to 152B to 152C.

*Leaves*.—Arrangement: Alternate, simple. Length: About 4.3 cm. Width: About 2.5 cm. Shape: Roughly ovate, three-lobed. Apex: Acute. Base: Attenuate. Margin: Palmately lobed and coarsely dentate, sinuses between lateral lobes divergent to parallel. Texture, upper surface: Moderately pubescent. Texture, lower surface: Densely pubescent. Venation pattern: Pinnate. Color: Developing leaves, upper surface: Close to N137A. Developing leaves, lower surface: Close to 137C. Fully expanded leaves, upper surface: Close to N137B; venation, close to 138A to 138B. Fully expanded leaves, lower surface: Close to 147B; venation, close to 138A. Petiole: Length: About 8 mm. Diameter: About 1.7 mm. Texture, upper and lower surfaces: Densely pubescent. Color, upper surface: Close to 146C. Color, lower surface: Close to 147C.

Inflorescence description:

*Appearance*.—Decorative inflorescence form; inflorescences borne on terminals above foliar plane; disc and ray florets arranged acropetally on a capitulum.

*Fragrance*.—Faintly fragrant, pungent.

*Flowering response*.—Long flowering period; under natural season conditions, plants flower continuously from mid-September to late October in Belgium.

*Postproduction longevity*.—Inflorescences maintain good color and substance for about three weeks in an outdoor nursery; inflorescences not persistent.

*Quantity of inflorescences*.—About 30 inflorescences develop per lateral branch; about 1,000 inflorescences per plant.

*Inflorescence bud*.—Height: About 8 mm. Diameter: About 8 mm. Shape: Broadly ovate. Color: Close to 138A.

*Inflorescence size*.—Diameter: About 4.1 cm. Depth (height): About 1.7 cm. Disc diameter: About 9 mm. Receptacle diameter: About 3 mm. Receptacle height: About 3 mm. Receptacle color: Close to 145B.

*Ray florets*.—Length: About 1.9 cm. Width: About 6 mm. Shape: Narrowly obovate to oblong. Apex: Obtuse to emarginate. Base: Cuneate. Margin: Entire. Aspect: About 70° from vertical. Texture, upper and lower surfaces: Smooth, glabrous; longitudinally ridged. Number of ray florets per inflorescence: About 120. Color: When opening, upper surface: Close to 167C and N167D; at the base, close to 150A to 150B. When opening, lower surface: Close to 184C; at the base, close to 150A to 150B. Fully opened, upper surface: Close to 164B; at the base, close to 150A to 150B; color does not change with development. Fully opened, lower surface: Close to 181B to 181D; at the base, close to 150A to 150B; color does not change with development.

*Disc florets*.—Length: About 1.1 cm. Diameter: About 1 mm. Shape: Tubular, filiform; apices narrowly acute. Texture, inner and outer surfaces: Smooth, glabrous. Number of disc florets per inflorescence: About 50 massed at the center of the inflorescence. Color, immature: Close to 178A to 178B and 180A; at the base, close to 150B. Color, mature: Close to 178A to 178B and 180A; at the base, close to 150B.

*Phyllaries*.—Number of phyllaries per inflorescence: About 24 arranged in about three whorls. Length: About 6 mm. Width: About 3 mm. Shape: Ovate. Apex: Bluntly acute. Base: Cuneate. Margin: Entire. Texture, upper surface: Smooth, glabrous. Texture, lower surface: Pubescent. Color, upper surface: Close to 143B; margins, close to 199A. Color, lower surface: Close to 138A; margins, close to 199A.

*Peduncles*.—Length, terminal peduncle: About 8 cm. Length, fourth peduncle: About 8.6 cm. Diameter: About 1.5 mm. Aspect: Erect to about 35° from vertical. Strength: Strong. Texture: Densely pubescent. Color: Close to 147B to 147C.

*Reproductive organs*.—Androecium: Not observed. Gynoecium: Present only on ray florets. Quantity: One pistil per floret. Pistil length: About 5 mm. Style length: About 4 mm. Style color: Close to N144B. Stigma shape: Cleft, decurrent. Stigma color: Close to 9C. Ovary color: Close to 144C to 144D.

*Seed/fruit*.—Seed and fruit production have not been observed.

Disease/pest resistance: Plants of the new *Chrysanthemum* have been observed to not be susceptible to Rust pathogens. Resistance to pests and other pathogens common to *Chrysanthemums* has not been observed on plants grown under commercial conditions.

Garden performance: Plants of the new *Chrysanthemum* have demonstrated excellent garden performance, are hardy to USDA Hardiness Zones 7 to 8 and will tolerate high temperatures of about 35° C.

It is claimed:

1. A new and distinct *Chrysanthemum* plant named 'Bronze San Remo Runner' as illustrated and described.

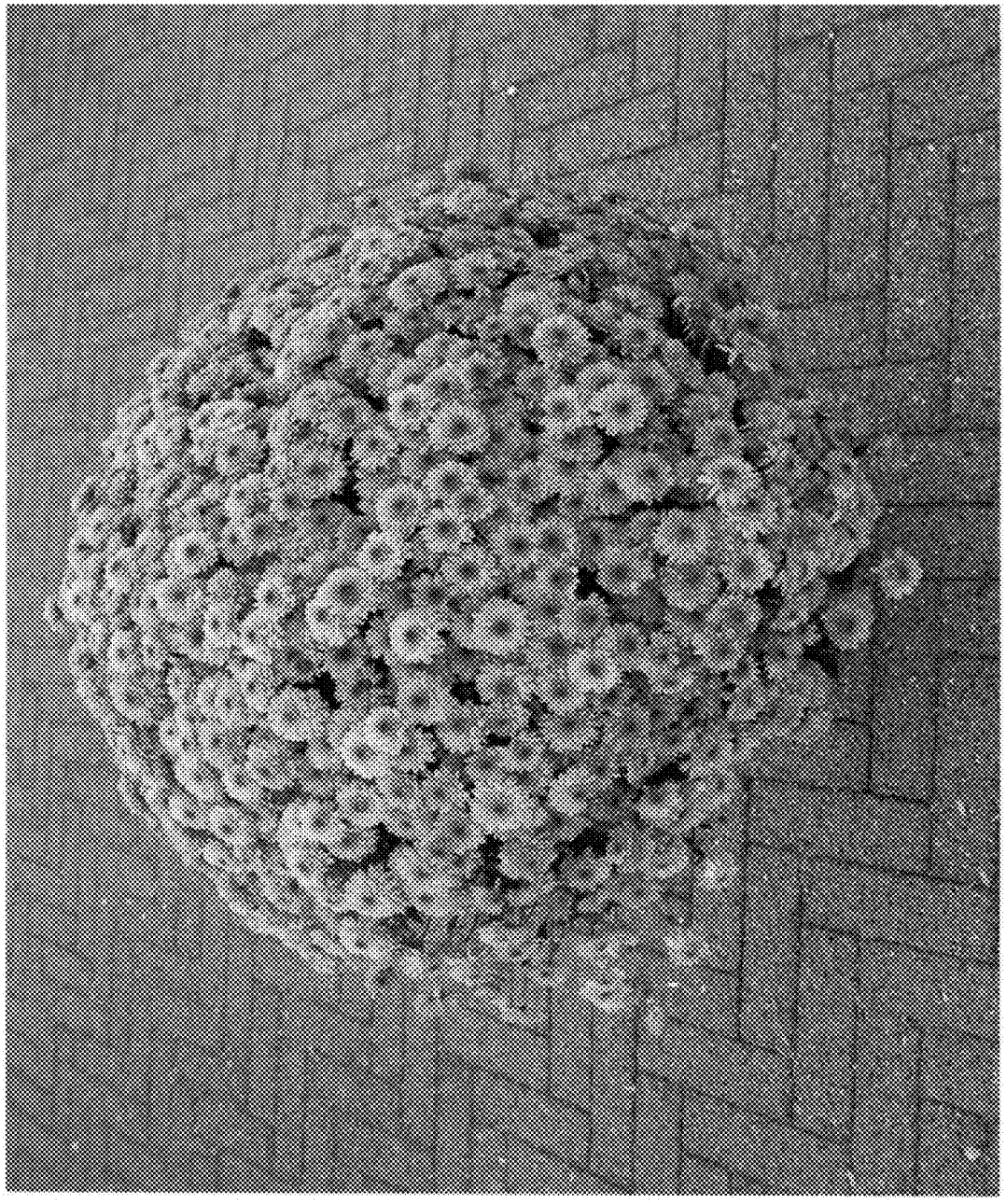

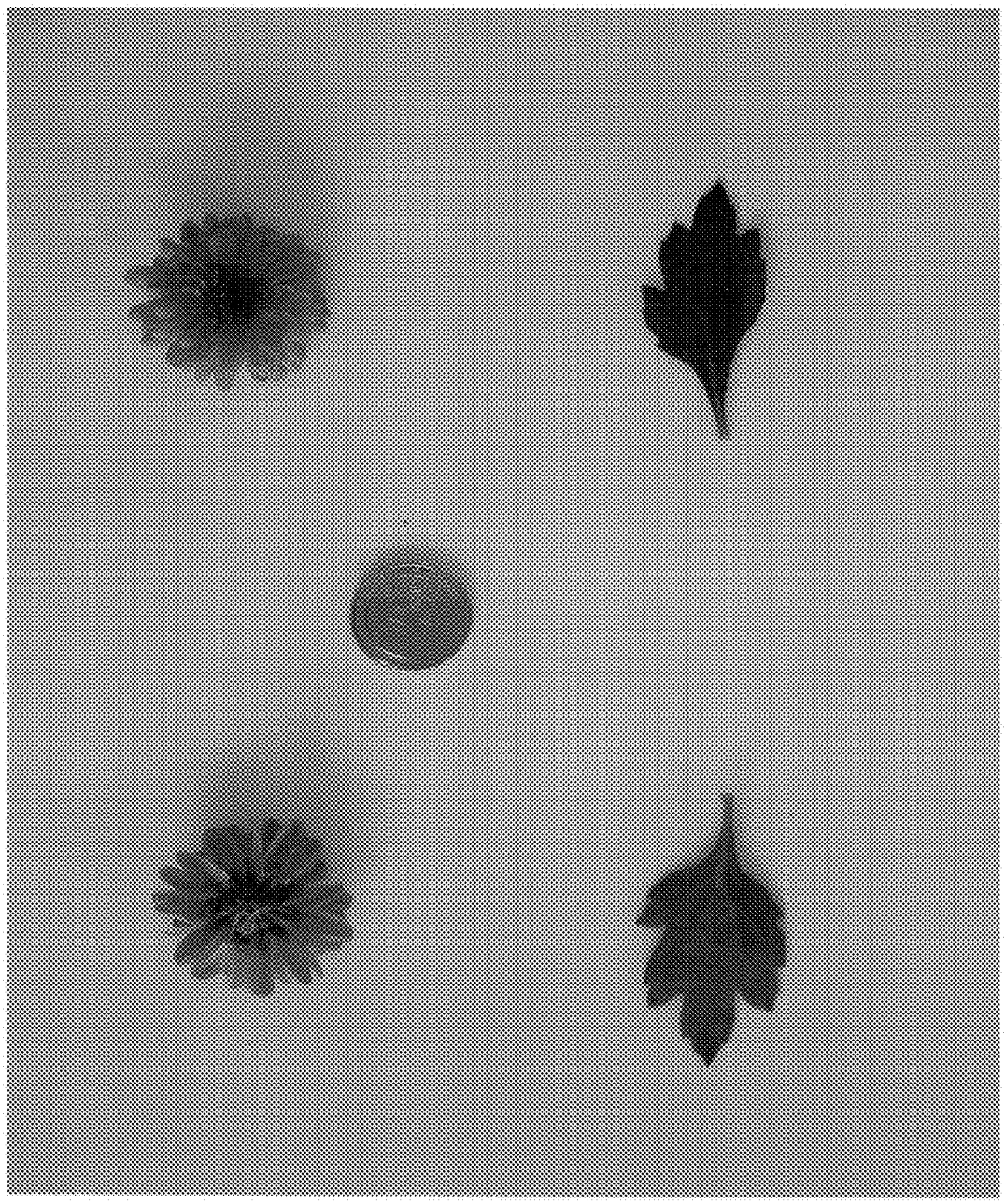

* * * * *